United States Patent [19]

Carminati et al.

[11] Patent Number: 4,542,136
[45] Date of Patent: Sep. 17, 1985

[54] 2-(1-PIPERAZINYL) PYRIMIDINES, THEIR SALTS AND PHARMACEUTICAL COMPOSITIONS CONTAINING THEM

[75] Inventors: Paolo Carminati, Milan, Italy; Kathleen Biziere, Clapiers; André Hallot, Saint Gely Du Fesc, both of France

[73] Assignee: Sanofi, Paris, France

[21] Appl. No.: 546,273

[22] Filed: Oct. 28, 1983

[30] Foreign Application Priority Data

Nov. 9, 1982 [FR] France ............................... 82 18819

[51] Int. Cl.$^4$ .................. A61K 31/505; C07D 403/04
[52] U.S. Cl. ..................................... 514/252; 544/295
[58] Field of Search ......................... 544/295; 424/251

[56] References Cited

U.S. PATENT DOCUMENTS 2,748,129 5/1956 Hofmann ............................. 544/295

Primary Examiner—Glennon H. Hollrah
Assistant Examiner—James H. Turnipseed
Attorney, Agent, or Firm—Stevens, Davis, Miller & Mosher

[57] ABSTRACT

The present invention relates to a process for preparing 2-(1-piperazinyl) pyrimidines of formula:

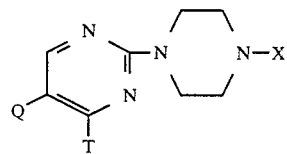

in which one of the groups T and Q represents hydrogen, a hydroxyl or lower alkanoyloxy group, and the other represents hydrogen; and X represents:
a group $-CO-R_1$
a group

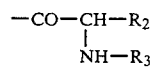

an alkylene-COOY group
an alkylene-CO—W group,
according to which a 2-(1-piperazinyl) pyrimidine of formula:

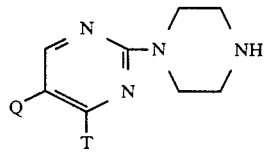

is reacted with a compound of formula AX in which A is selected from an atom of halogen and an activator group of the carboxylic function of the radical X.

3 Claims, No Drawings

2-(1-PIPERAZINYL) PYRIMIDINES, THEIR SALTS AND PHARMACEUTICAL COMPOSITIONS CONTAINING THEM

The present invention relates to novel 2-(1-piperazinyl)pyrimidines having a dopaminergic psychotherapeutic activity, to salts thereof, to a process for preparing them as well as to pharmaceutical compositions containing them as active ingredients.

More particularly, the invention relates to 2-(1-piperazinyl)pyrimidines of formula:

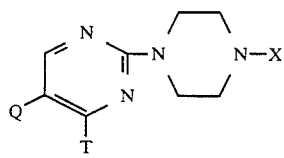

in which one of T and Q represents hydrogen, a hydroxyl or lower alkylcarbonyl group and the other represents hydrogen; and X represents:
a group CO—$R_1$ where $R_1$ is a lower alkyl
a group

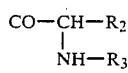

where $R_2$ is hydrogen, or a lower alkyl, phenyl, p-hydroxyphenyl, benzyl, p-hydroxybenzyl, hydroxymethyl, 1-hydroxyethyl or 3-indolylmethyl group and $R_3$ is hydrogen, a lower alkylcarbonyl, a benzoyl or an acyl group derived from an amino acid selected from: glycine, phenylglycine, alanine, valine, leucine, isoleucine, phenylalanine, tryosine, serine, threonine or tryptophane, or an acyl group derived from a dipeptide constituted from two of the amino acids mentioned above or $R_2$ and $R_3$ taken together form an ethylene group;
a group Alk—COOY, where Alk represents an alkylene group with straight or branched chain having from 1 to 4 carbon atoms and Y is hydrogen or a lower alkyl;
a group Alk—$CH_2$ OZ, where Alk is as defined hereinabove and Z is hydrogen, or a lower alkyl, (lower alkoxy)-lower alkyl, lower alkylcarbonyl group;
a group Alk—CO—W where Alk is as defined hereinabove and W is a lower alkyl group,
as well as to the pharmaceutically acceptable acid addition salts thereof.

The term "lower alkyl" as used here designates a radical derived from a saturated aliphatic hydrocarbon containing 1 to 4 carbon atoms, such as methyl, ethyl, propyl, isopropyl, n-butyl and the like.

The term "lower alkoxy" designates the hydroxyl group substituted by a lower alkyl such as defined above.

The term "lower alkylcarbonyl" designates a radical

in which R is a lower alkyl radical.

Compounds (I) according to the present invention are prepared in accordance with the reaction diagram:

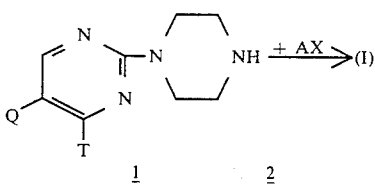

Compounds (I) are generally obtained by substitution on the nitrogen atom of 2-(1-piperazinyl)pyrimidine 1 by a derivative AX of the substituent X to be introduced. Most often, A designates an atom of halogen and preferably chlorine or bromine.

In this case, substitution is carried out within an inert solvent such as dimethylformamide or dimethylsulfoxide in the presence of an inorganic alkaline agent such as sodium carbonate, or organic such as triethylamine at a temperature of between 80° C. and the temperature of boiling of the solvent.

Where X represents a group

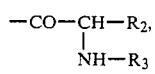

substitution is effected with the acid

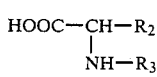

and in this case A represents an activator group of the carboxylic function and in particular the activator groups usually used in peptide chemistry such as the activated esters of paranitrophenyl or N-hydroxysuccinimide or mixed anhydrides with ethyl chloroformate or with isobutyl chloroformate.

Substitution may also be carried out with the acid itself, operating in the presence of a carbodiimide and in particular dicyclohexylcarbodiimide.

For substitution to be effected univocally, it is necessary, where $R_3$ represents hydrogen, to block the primary amine function by a protector group which is easy to eliminate subsequently, such as benzyloxycarbonyl or tertiobutyloxycarbonyl groups.

Moreover, when substituent $R_2$ contains one or more groups capable of reacting in the course of the reaction of substitution, and particularly hydroxyl groups, it is preferable to block these substituents by a protector group which is easy to eliminate subsequently. In the case of the hydroxyl groups, a benzyl ether group may in particular be used.

Finally, when $R_3$ represents an acyl group derived from an aminoacid or a peptide, the assembly of the substituent

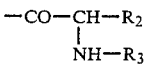

may either be introduced directly as indicated previously or the substituent

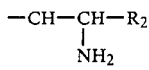

may be introduced according to the same process, then the peptide chain may be extended with one or two other aminoacids. In this case, the functions NH2 and OH of R3 which are possibly present must be selectively blocked as indicated above.

The compounds of formula I hereinabove as well as their pharmaceutically acceptable salts have a very good psychotherapeutic activity with a mechanism of dopaminergic action which allows them to be used as drugs in pharmaceutical compositions for the treatment of psychic, neurological and neuromuscular disorders in mammals, including humans.

The dopaminomimetic activity of the products of the invention has been studied on the striatal dopaminergic receptors of the mouse in accordance with the technique described by P. PROTAIS and J. COSTENTITN, Journal de Pharmacologie (Paris), 7, 251-255 (1976). The unilateral lesion of the nigrostriatal dopaminergic neurones induces a hypersensitivity of the receptors of the dopamine at the level of the striatum. The resulting asymmetry is revealed by rotations of the animal in the direction contralateral to the receptors most intensely stimulated. After administration of the products to be studied (0.1 mg/kg of body weight by the oral route), the number of turns made by the animal is counted for a period of 2 minutes. The results are expressed in the form of percentage of variations with respect to the controls not having received products.

Counting is effected 3 hours after administration of the products and is repeated after 6 hours. Under these conditions, the following results were obtained:

| SR 41697 A | 3 hours: −86% | 6 hours: −105% |
|---|---|---|
| SR 41902 A | 3 hours: −71% | 6 hours: −71% |

In the pharmaceutical compositions of the present invention for oral, sublingual, subcutaneous, intramuscular, intravenous, transdermic or rectal administration, the active ingredients of formula I hereinabove may be administered in unitary forms of administration, mixed with conventional pharmaceutical supports, to animals and human beings for the treatment of disorders of the mood or the behaviour, particularly in the case of psychoses, depression, states of anxiety and insomnias. Among the appropriate unitary forms of administration, there are the forms by the oral route such as tablets, capsules, powders, granules and oral solutions or suspensions and the forms of parenteral administration useful for subcutaneous, intramuscular or intravenous administration.

In order to obtain the desired psychotherapeutic effect, the dose of active ingredient may vary between 0.1 and 100 mg per kg of body weight and per day. Each unitary dose may contain from 1 to 300 mg of active ingredient in combination with a pharmaceutical support. This unitary dose may be administered 1 to 4 times per day for treating disorders of the mood or the behaviour.

The following non-limiting examples enable the scope of the invention to be more readily understood.

EXAMPLE 1

2-(4-propionyl 1-piperazinyl)pyrimidine (SR 41682)

(I) T=Q=H; X=—COCH2CH3

5.6 g of acid maleate of 2-(1-piperazinyl)pyrimidine are dissolved in 80 ml of dimethylformamide, then 5.6 ml of triethylamine and 3.8 g of 3,4-methylenedioxy benzoyl chloride are added. The mixture is heated for 12 hours at 130° C. then the solvent is evaporated to dryness in vacuo. The residue is taken up in a dilute solution of hydrochloric acid and washed with ether. The aqueous phase is rendered alkaline by a sodium carbonate solution and extracted with ethyl acetate. The solution is dried over sodium sulfate and the solvent is evaporated to dryness.

The residue is chromatographed over silica gel. By eluting with ethyl acetate, the expected product is obtained. It is recrystallized in isopropyl ether to obtain crystals (2.6 g). m.p.: 98°-100° C.

EXAMPLE 2

2-(4-ethoxycarbonylmethyl 1-piperazinyl)pyrimidine, hydrochloride (SR 41697A)

(I) T=Q=H; X=—CH2COOC2H5

Operation is carried out as in Example 1, replacing the propionyl chloride by an equivalent quantity of ethyl bromacetate.

After heating to 140° C. for 6 hours, the expected product is isolated as indicated in Example 1. After chromatography, the product remains oily. It is transformed into hydrochloride by adding to the solution of the base in ether an excess of a solution of hydrochloric gas in the same solvent.

The crystals are drained and recrystallized twice in absolute ethanol. m.p.: higher than 260° C.

EXAMPLE 3

2-(4-acetonyl 1-piperazinyl)pyrimidine, hydrochloride (SR 41722A)

(I) T=Q=H; X=CH2COCH3

To the solution of 5.6 g of acid maleate of 2-(1-piperazinyl)pyrimidine in 100 ml of dimethylsulfoxide are added 10.6 g of sodium carbonate and 1.3 ml of chloroacetone, then the mixture is heated to 110° C. for 4 hours.

The solvent is evaporated to dryness in vacuo and the residue is taken up in the minimum of salt water and extracted with ethyl acetate. The solution is dried and the solvent is evaporated in vacuo. The residue is chromatographed over silica gel. By eluting with ethyl acetate, an impurity is eliminated, then, by eluting with the ethyl acetate/methanol (90-10) vol/vol mixture, the expected product is obtained in the form of oil.

The hydrochloride is made in ether then recrystallized twice in absolute ethanol.

A hygroscopic solid is finally obtained.
m.p.: higher than 260° C.

EXAMPLE 4

2-[4-(L-prolyl-L-lencyl-glycyl) 1-piperazinyl]pyrimidine, trifluoroacetate (SR 41902 A)

(I) T=2=H; X=-Gly-Leu-Pro (a) Boc-Leu-Gly-OMe

To the solution of 5.02 g of hydrochloride of the methyl ester of glycine in a mixture of 20 ml of dichloromethane and 30 ml of dimethylformamide, cooled to 0° C., there are added 5 ml of N-ethylmorpholine then the solution of 9.5 g of dry Boc-Leucine in 50 ml of dichloromethane. 9.04 g of dicyclohexylcarbodiimide, 6 g of 1-hydroxy benzotriazol and 1.5 ml of N-ethylmorpholine are then added. After 45 minutes at 0° C., the mixture is stirred for 5 hours at ambient temperature. The insoluble is filtered and washed with ethyl acetate. The filtrate is diluted with 700 ml of ethyl acetate and the organic solution is washed 3 times with an aqueous solution of sulfate and potassium bisulfate, then 3 times with a saturated sodium bicarbonate solution and finally 3 times with a saturated sodium chloride solution. The organic solution dried over sodium sulfate is concentrated in vacuo to 200 ml. 150 ml of hexane are added and the mixture is left to crystallize, drained and washed with hexane.

Crystals are thus obtained (9.90 g).

$[\alpha]_D^{20} = -20.3°$ (c=1 dimethylformamide).

(b) Trifluoroacetate of H-Leu-Gly-OMe 5 g of the peptide obtained in (a) in the mixture of 20 ml of dichloromethane and 20 ml of trifluoroacetic acid are stirred for 35 minutes. The mixture is evaporated to dryness in vacuo then the residue is taken up in 150 ml of ether, evaporated to dryness. An oily product is obtained (7 g) used as such for the following step.

(c) Boc-Pro-Leu-Gly-OMe

To the product obtained in (b) (7 g) dissolved in 55 ml of dichloromethane, N-ethylmorpholine is added to bring the pH towards 6. 3.55 g of Boc-Proline, 3.70 g of dicyclohexylcarbodiimide, 2.60 g of 1-hydroxy benzotriazol and again N-ethylmorpholine are then added to return the pH towards 6. The mixture is left for 2 hrs. 30 mins. at ambient temperature then the insoluble is filtered and washed with ethyl acetate. The filtrate diluted with 500 ml of ethyl acetate is washed as indicated in paragraph (a). The solution is dried over sodium sulfate then concentrated to 100 ml in vacuo. 100 ml of hexane are added and the precipitate is drained. The solid dissolved in chloroform is chromatographed over a silica column (100 g). By eluting by the chloroform-methanol (97-3) vol/vol mixture, the expected product is obtained. After evaporation of the solvent, the product is taken up in ethyl acetate and precipitated by addition of ether and hexane. A solid is obtained (4.45 g).

m.p.: 103°–105° C. $[\alpha]_D^{20} = -59°$ (c=1 dimethylformamide)

(d) Boc-Pro-Leu-Gly-OH

To the solution of 4.8 g of the product obtained above in 10 ml of methanol and 10 ml of dioxane, 6 ml of 1N sodium hydroxide solution are added. After 15 minutes, 6 ml of 1N sodium hydroxide solution are again added and the mixture is left for 45 minutes. 2 ml of the same sodium hydroxide solution are added and the mixture is left for 2 hours. 50 ml water and 100 ml of ethyl acetate are added and the mixture is acidified to pH=2 by a saturated solution of potassium bisulfate. The organic phase is separated and the aqueous phase is reextracted with 500 ml of ethyl acetate. The organic extracts are collected and washed with a solution of sulfate-potassium bisulfate then with a saturated solution of sodium chloride.

The solution is dried over sodium sulfate and concentrated to dryness in vacuo. The residue is redissolved in 50 ml of ethyl acetate and 150 ml of hexane are added. The mixture is cooled for one hour in the refrigerator and the crystals formed are drained and washed with hexane.

Weight: 4.2 g; m.p.: 95°–96° C. $[\alpha]_D^{20} = -81°$ (c=1 methanol)

(e) 2-[4-(Boc-Pro-Leu-Gly) 1-piperazinyl]pyrimidine

To the solution of 1.6 g of 2-(1-piperazinyl)pyrimidine in 50 ml of dichloromethane are added 3.75 g of the tripeptide obtained in (d) then 2.20 g of dicyclohexylcarbodiimide, 1.50 g of 1-hydroxy benzotriazol and 1.2 ml of N-ethylmorpholine. The mixture is left to react for 4 hours and the precipitate is filtered and washed three times with 30 ml of ethyl acetate. The filtrate is diluted by 600 ml of ethyl acetate and washed twice with an 0.5N sodium hydroxide solution then four times with a saturated sodium chloride solution. The mixture is dried over sodium sulfate and concentrated in vacuo. The residue is dissolved in 20 ml of ethyl acetate and 5 ml of chloroform. 150 ml of ether are added and left for 30 minutes. The crystals are drained and washed with ether. In this way, 4.15 g of the expected product are obtained $[\alpha]_D^{20} = -78.3°$ (c=1 methanol).

(f) SR 41902 A 4.08 g of the product obtained above are shaken with 15 ml of dichloromethane, 1.5 ml of anisole and 18 ml of trifluoroacetic acid for 35 minutes. The mixture is concentrated in vacuo to a volume of 7 to 8 ml and is poured in 150 ml of ether. A gum is obtained which is decanted and washed by decantation with 20 ml of ether. It is evaporated in vacuo and the residue is redissolved in 150 ml of water and Amberlite IR 45 (RTM) resin is added in OH⁻ form up to about pH 8. The resin is filtered and washed twice with 50 ml of water. The aqueous phase is concentrated up to 30 ml then the residue is lyophilized. A white solid (2.9 g) is obtained.

$[\alpha]_D^{20} = -50°$ (c=1 water)

Analysis of amino acids: Pro=0.9, Gly=1.03, Leu=0.97. Chromatography over thin layer of silica. Rf.=0.3 (chloroform, methanol, acetic acid (80-17-13) vol/vol).

EXAMPLE 5

Capsules based on one of the compounds of Examples 1 to 4 are prepared, having the following composition:

| active principle | 15 mg |
|---|---|
| lactose | 120 mg |
| magnesium stearate | 5 mg | by intimately mixing charges of the above ingredients and pouring the mixture into capsules of hard gelatin.

EXAMPLE 6

Tablets based on one of the compounds of Examples 1 to 4 are prepared, having the following composition:

| active ingredient | 20 mg |
|---|---|
| lactose | 100 mg |
| microcrystalline cellulose | 30 mg |
| dried corn starch | 40 mg |
| magnesium stearate | 5 mg | by grinding the active ingredient to a particle size of 0.4 mm, by passing it through a sieve of 0.4 mm mesh, mixing the ground matter with the other constituents and compressing to form tablets.

In the same way, tablets are prepared containing 40 mg of active ingredient.

EXAMPLE 7

By operating as described in Example 6 above, tablets are prepared, having the following composition:

| active principle | 50 mg |
| --- | --- |
| lactose | 95 mg |
| corn starch | 100 mg |
| talc | 4.5 mg |
| magnesium stearate | 0.5 mg |

EXAMPLE 8

Suppositories are prepared having the following composition:

| active principle | 50 mg |
| --- | --- |
| lactose | 250 mg |
| witepsol W 45 q.s.p. | 1.7 mg |

The active substance is mixed with the lactose and the mixture is placed uniformly in suspension in the molten mass for suppositories. The suspension is poured in cooled moulds to form suppositories weighing 1.7 g.

What is claimed is:

1. 2-(1-piperazinyl)pyrimidines of formula:

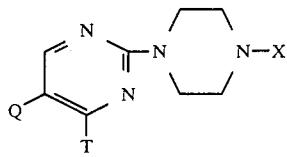

in which one of radicals T and Q represents hydrogen, a hydroxyl or lower alkylcarbonyl group and the other represents hydrogen; and X represents:

a group CO—$R_1$ where $R_1$ is a lower alkyl a group $$CO-\underset{\underset{NH-R_3}{|}}{CH}-R_2$$

where $R_2$ is hydrogen, or a lower alkyl, phenyl, p-hydroxyphenyl, benzyl, p-hydroxybenzyl, hydroxymethyl, 1-hydroxyethyl or 3-indolylmethyl group and $R_3$ is hydrogen, a lower alkylcarbonyl, a benzoyl or an acyl group derived from an amino acid selected from: glycine, phenylglycine, alanine, valine, leucine, isoleucine, phenylalanine, tyrosine, serine, threonine or tryptophane, or an acyl group derived from a dipeptide constituted from two of the amino acids mentioned above or $R_2$ and $R_3$ taken together form an ethylene group;

a group Alk—COOY, where Alk represents an alkylene group with straight or branched chain having from 1 to 4 carbon atoms and Y is hydrogen or a lower alkyl;

a group Alk—$CH_2$ OZ, where Alk is as defined hereinabove and Z is hydrogen, or a lower alkyl, (Lower alkoxy)-lower alkyl, lower alkylcarbonyl group;

a group Alk—CO—W where Alk is as defined hereinabove and W is a lower alkyl group, as well as the pharmaceutically acceptable acid addition salts thereof.

2. Pharmaceutical compositions useful in the treatment of psychic, neurological and neuromuscular disorders, comprising an effective amount of at least one active ingredient within the scope of claim 1, in association with a pharmaceutically acceptable carrier.

3. Pharmaceutical compositions of claim 2 when prepared in dosage unit form, containing from 1 to 300 mg of said active ingredient.

* * * * *